United States Patent [19]

Burger et al.

[11] 3,996,272

[45] Dec. 7, 1976

[54] METHOD FOR PREPARING PENTACHLOROACETONE AND DICHLOROACETIC ACID FROM ISOPROPYL ETHERS

[75] Inventors: Joanne D. Burger; William L. Howard, both of Lake Jackson, Tex.

[73] Assignee: The Dow Chemical Company, Midland, Mich.

[22] Filed: Oct. 3, 1974

[21] Appl. No.: 511,842

[52] U.S. Cl. .................. 260/539 A; 204/158 HA; 260/593 H
[51] Int. Cl.$^2$ .................. C07C 53/16; C07C 49/08
[58] Field of Search .................. 260/539 A, 593 H

[56] References Cited

UNITED STATES PATENTS

| 1,391,757 | 9/1921 | Buc | 260/593 H |
| 2,199,934 | 5/1940 | Heisel | 260/593 H |
| 2,695,918 | 11/1954 | Gilbert et al. | 260/539 A |

FOREIGN PATENTS OR APPLICATIONS

| 43-19927 | 8/1968 | Japan | 260/539 A |

OTHER PUBLICATIONS

Hall et al., J.A.C.S., 74, (1952) p. 836.
Edwards et al., J. Chem. Soc., (1944), pp. 1942–1946.
Vilsmaier, Liebigs Ann. Chem., 735, (1970), pp. 23–26.
Kulka, Chem. Abst., 45:4646: (1951).
Roberts et al., *Basic Principles of Organic Chemistry*, (1965) pp. 201–202.

*Primary Examiner*—Lorraine A. Weinberger
*Assistant Examiner*—Michael Shippen
*Attorney, Agent, or Firm*—Raymond B. Ledlie

[57] ABSTRACT

This invention relates to a chemical process for preparing pentachloro-2-propanone (pentachloroacetone) and dichloroacetic acid from isopropyl ethers which may be partially chlorinated. The pentachloroacetone process is carried out by reacting the isopropyl ethers with chlorine in the presence of water to produce pentachloroacetone which can then be recovered. Alternatively, if dichloroacetic acid is desired, the pentachloroacetone process may be carried further by reacting the pentachloroacetone with a base-acting material to produce a salt of dichloroacetic acid and then reacting this salt with acid to produce dichloroacetic acid of about 95% purity.

32 Claims, No Drawings

METHOD FOR PREPARING PENTACHLOROACETONE AND DICHLOROACETIC ACID FROM ISOPROPYL ETHERS

BACKGROUND OF THE INVENTION

Prior to this invention there were several known methods for the preparation of both pentachloro-2-propanone, hereinafter referred to as pentachloroacetone, and dichloroacetic acid, but none of these employed the novel process of this invention.

One of the known methods for preparing pentachloroacetone is the chlorination of isopropyl alcohol as disclosed in Hyym E. Buc., U.S. Pat. No. 1,391,757 (1927). Another is the chlorination of acetone in sunlight as pointed out in Huntress, *Organic Chlorine Compounds*, p. 812, John Wiley & Sons, Inc., New York, (1948). A commonly used method for the production of dichloroacetic acid is the chlorination of acetic acid. However, this method produces significant proportions of by-products including monochloroacetic and trichloroacetic acid which pose difficult separation problems for the isolation of the dichloroacetic acid; e.g., fractional distillation is difficult due to the closeness of the boiling points of these acids. Elaborate separation methods have been devised by others to alleviate this problem. None of these methods have proven completely satisfactory.

The process of this invention avoids the acid separation problem because it produces 95% pure dichloroacetic acid in high yields which is virtually free of the other chlorinated acetic acids.

A further advantage of this invention is that it readily allows utilization of di(chloroisopropyl) ether as a source material, such ether currently being a waste product of certain industrial processes.

The above advantages as well as others are now achievable because it has now been discovered that both pentachloroacetone and dichloroacetic can be prepared from certain isopropyl ethers. Pentachloroacetone is produced by chlorinating these ethers in the presence of water. Dichloroacetic acid is produced by chlorinating these ethers in the presence of water to produce pentachloroacetone, reacting this pentachloroacetone with an inorganic base-acting material to produce a salt of the dichloroacetic acid, and reacting this salt with a strong mineral acid.

More specifically the process of this invention can be described as follows.

Pentachloroacetone is produced by reacting chlorine in the presence of water with at least one of the isopropyl ethers having either the formula $C_3H_{(7-x)}Cl_x$—O—$C_3H_{(7-y)}Cl_y$ or $C_3H_{(7-x)}Cl_x$—O—R or a mixture thereof, where x and y are integers independently selected from those integers from zero to five, inclusive, and R is selected from the group consisting of lower alkyl groups and chlorinated lower alkyl groups where lower alkyl is defined as an alkyl containing from 1 to 6 carbon atoms. This chlorination step is carried out at a temperature of from about 25° to about 300° C and a pressure of from about 0.5 to about 10 atmospheres for a time sufficient to produce an optimum amount of pentachloroacetone, such time being from as low as aboout 2 to about 6 hours to as high as about 60 hours. The chlorine to ethers molar ratio for this chlorination step is not so critical as to require one specific ratio, but in order to prevent substantial underchlorination or overchlorination, both of which reduce the pentachloroacetone yield, a molar ratio should be used which produces acceptable yields. For ethers having the formula $C_3H_{(7-x)}Cl_x$—O—$C_3H_{(7-y)}Cl_y$, the theoretical number of moles of chlorine needed per mole of ether is given by the mathematical expression $[(6-x) + (6-y)]$, where x and y have the same numerical value as they do in the formula for the ether. For those ethers having the general formula $C_3H_{(7-x)}Cl_x$—O—R, the theoretical number of moles of chlorine required per mole of ethers is given by the mathematical term $(6-x)$, where x has the same numerical value as it does in this ether general formula. However, acceptable yields result when molar ratios other than the theoretical ratios are used. For example, di(chloroisopropyl) ether, $C_3H_6Cl$—O—$C_3H_6Cl$, produces acceptable yields when using a chlorine to ether molar ratio of from about 8:1 to about 20:1 while a molar ratio of from about 10:1 to about 14:1 is preferred. It may be noted that the theoretical ratio would be 10:1 for this particular ether, with $x=1$ and $y=1$.

The ethers represented by the general formula $C_3H_{(7-x)}Cl_x$—O—$C_3H_{(7-y)}Cl_y$, are acceptably chlorinated with a chlorine to ether mole ratio of from about $0.8[(6-x) + (6-y)]:1$ to about $2[(6-x) + (6-y)]:1$ with a preferred ratio of from about $[(6-x)+(6-y)]:1$ to about $1.4](6-x)+(6-y)]:1$, where x and y are integers independently selected from zero to five, but each having the same numerical value in the ratio as they do in the particular ether or mixtures of ethers being chlorinated.

For the ethers represented by the general formula $C_3H_{(7-x)}Cl_x$—O—R, acceptable chlorination of the isopropyl group occurs when the molar ratio of chlorine to ether is from about $0.8(6-x):1$ to about $2(6-x):1$ with a preferable ratio being about $(6-x):1$ to about $1.4(6-x):1$ where x is an integer from zero to 5, but being the same in the particular ether or ethers chlorinated as in the ratio, and R is selected from lower alkyl or chlorinated lower alkyl groups. The molar ratios above do not include the extra chlorine that is required if R reacts with the chlorine. An allowance would have to be made for this extra chlorine, with the molar ratio values of chlorine to ether increased accordingly to compensate therefor.

There is sufficient time during this chlorination step to determine when the optimum or other desired amount of pentachloroacetone is attained by methods such as gas chromatographic analysis. Once the desired amount is determined along with the time it took to achieve this amount, subsequent runs can be made without the gas chromatography by merely using the predetermined reaction time. Overchlorination results in excess production of hexachloroacetone which immediately breaks down into chloroform and carbon dioxide since it is unstable under these reaction conditions. Underchlorination yields more tetra-, tri-, di-, and even some monochloroacetone depending upon the extent of the underchlorination. By chlorinating the isopropyl ethers until there is virtually no mono-, di-, tri-, nor tetrachloroacetone remaining the only chlorinated acetone present in substantial quantities is pentachloroacetone since hexachloroacetone is unstable under the reaction conditions.

Without the presence of the other chlorinated acetones, pentachloroacetone can be readily converted to dichloroacetic acid of high purity in good yields and with insignificant amounts of mono- or trichloroacetic acid being present.

If dichloroacetic acid is desired, it is prepared by a process which comprises using the identical process for the production of pentachloroacetone described above, taking the pentachloroacetone thus produced and reacting it with a fairly strong base-acting material such as sodium hydroxide to produce a salt of dichloroacetic acid, and then reacting this salt with a strong mineral acid such as HCl to produce dichloroacetic acid. The base-acting material is a member selected from a group consisting of alkali metal hydroxides, alkaline earth metal hydroxides, alkali metal carbonates, and mixtures thereof.

SUMMARY OF THE INVENTION

It has now been discovered that pentachloroacetone can be prepared from certain isopropyl ethers by a process which comprises reacting chlorine in the presence of water with at least one isopropyl ether having the formula $C_3H_{(7-x)}Cl_x$—O—$C_3H_{(7-y)}Cl_y$ or the formula $C_3H_{(7-x)}Cl_x$—O—R, where $x$ and $y$ are integers independently selected from zero to five inclusive and R is selected from lower alkyl groups or chlorinated lower alkyl groups at a temperature of from about 25° to about 300° C and a pressure of from about 0.5 to about 10 atmospheres.

An alternative embodiment of the invention is the preparation of dichloroacetic acid by a process which comprises:

a. reacting chlorine in the presence of water with at least one isopropyl ether having the formula $C_3H_{(7-x)}Cl_x$—O—$C_3H_{(7-y)}Cl_y$ or the formula $C_3H_{(7-x)}Cl_x$—O—R, where $x$ and $y$ are integers independently selected from zero to five and R is selected from lower alkyl groups or chlorinated lower alkyl groups at a temperature of from about 25° to about 300° C and a pressure of from about 0.5 to about 10 atmospheres to produce pentachloroacetone;

b. reacting the thus formed pentachloroacetone with an inorganic base-acting material to produce a salt of dichloroacetic acid; and c. reacting the thus produced salt of dichloroacetic acid with a mineral acid to produce dichloroacetic acid.

DETAILED DESCRIPTION OF THE INVENTION

The process of this invention pertains to a novel process for the production of pentachloroacetone and dichloroacetic acid from certain isopropyl ethers which may be partially chlorinated, and in particular from di(chloroisopropyl) ether. The ethers to which this process is applicable are those partially and non-chlorinated isopropyl ethers having the formula $C_3H_{(7-x)}Cl_x$—O—$C_3H_{(7-y)}Cl_y$ or the formula $C_3H_{(7-x)}Cl_x$—O—R, or a mixture thereof, where $x$ and $y$ are independently selected from the integers zero to five, inclusive, and R is selected from any lower alkyl or chlorinated lower alkyl group, preferably containing 6 or less carbon atoms. Only the isopropyl groups of these ethers are useful in the preparation of pentachloroacetone or dichloroacetic acid by the process of this invention. Ethers containing only one isopropyl group are usable in this process; however they are generally considerably less efficient in the production of pentachloroacetone and dichloroacetic acid since the non isopropyl group as well as the isopropyl group of the ether reacts with the reagents used without contributing to the production of either pentachloroacetone or dichloroacetic acid.

The process of this invention is carried out in a sequence of steps. If dichloroacetic acid is desired pentachloroacetone is first produced by the chlorination in the presence of water of one of the ethers defined above or a mixture thereof. The pentachloroacetone thus produced is then reacted with an inorganic base-acting material selected from a group consisting of alkali metal hydroxides, alkaline earth metal hydroxides, alkali metal carbonates, and mixtures thereof to produce a salt or salts of dichloroacetic acid. The salt is then reacted with a strong mineral acid to produce dichloroacetic acid which can be isolated from the reaction mixture by known methods. However, if pentachloroacetone is the desired product, the process for producing it comprises the chlorinating step defined above for the preparation of dichloroacetic acid without the additional base-acting material and acid reaction steps.

In chlorinating the ether to produce pentachloroacetone, temperature, pressure, and time are not critical but it is usually desirable to conduct this reaction at a pressure of from about 0.5 to about 10 atmospheres, at a temperature of from about 25° to about 300° C, and for a time sufficient to produce the pentachloroacetone which is usually not less than from about 2 to about 6 hours.

However, it is generally preferable to employ pressures of from about 1 to about 5 atmospheres and temperatures of from about 100° to about 200° C. At pressures below one atmosphere the process would require expensive vacuum equipment, and there is no particular advantage for operating above 5 atmospheres. At temperatures below 100° C the rate of reaction becomes slower while degradation of product begins occurring at temperatures about 200° C.

It has unexpectedly been found that the presence of water is essential during the chlorination of the ether for without it the chlorination will cease before an appreciable amount of pentachloroacetone is produced, leaving instead a complex mixture of chlorinated ethers. The minimum amount of water necessary is that proportion which is sufficient to maintain aqueous saturation in the organic phase and to provide a sufficient amount of aqueous phase to give practical rates of operation. Beyond this required minimum proportion of water the ratio of water to ether is not critical, but it is usually practical to employ a range of from about 0.2 to 1 to about 10 to 1 (water to ether) with a preferred ratio of from about 0.5 1 to about 2.5 to 1 and an optimum ratio of about 1 to 1.

It has also been found that intimately admixing the organic and aqueous phases as well as irradiation of the reaction mixture with actinic light such as ultraviolet light during the chlorination increases the reaction rate. It is convenient to carry out the chlorination under reflux in order to return to the reaction mixture any chlorine and condensible vapors that have been carried from it by the hydrogen chloride off-gas. Alternatively the off-gas may be collected and processed elsewhere for the recovery of these values.

The chlorine to ether molar ratio for this chlorination step is not so critical as to require one specific ratio, but in order to prevent substantial underchlorination or overchlorination, both of which reduce the pentachloroacetone yield, a molar ratio should be used which produces acceptable yields. For ethers having the formula $C_3H_{(7-x)}Cl_x$—O—$C_3H_{(7-y)}Cl_y$, the theoretical number of moles of chlorine needed per mole of ether is given by the mathematical expression $[(6-x) + (6-y)]$, where $x$ and $y$ have the same numerical value as they do in the formula for the ether. For those ethers having the general formula $C_3H_{(7-x)}Cl_x—O—R$, the theoretical number of moles of chlorine required per mole of ether is given by the mathematical term $(6-x)$, where $x$ has the same numerical value as it does in this ether general formula. However, acceptable yields result when molar ratios other than the theoretical ratios are used. For example, di(chloroisopropyl) ether, $C_3H_6Cl—O—C_3H_6Cl$, produces acceptable yields when using a chlorine to ether molar ratio of from about 8:1 to about 20:1 while a molar ratio of from about 10:1 to about 14:1 is preferred. It may be noted that the theoretical ratio would be 10:1 for this particular ether, with $x=1$ and $y=1$.

The ethers represented by the general formula $C_3H_{(7-x)}Cl_x—O—C_3H_{(7-y)}Cl_y$ are accceptably chlorinated with a chlorine to ether mole ratio of from about $0.8[(6-x) + (6-y)]:1$ to about $2[(6-x) + (6-y)]:1$ with a preferred ratio of from about $[(6-x) + (6-y)]:1$ to about $1.4[(6-x) + (6-y)]:1$, where $x$ and $y$ are integers independently selected from zero to five, but each having the same numerical value in the ratio as they do in the particular ether or mixtures of ethers being chlorinated.

For the ethers represented by the general formula $C_3H_{(7-x)}Cl_x—O—R$, acceptable chlorination of the isopropyl group occurs when the molar ratio of chlorine to ether is from about $0.8(6-x):1$ to about $2(6-x):1$ with a preferable ratio being about $(6-x):1$ to about $1.4(6-x):1$ where $x$ is an integer from zero to 5, but being the same in the particular ether or ethers chlorinated as in the ratio, and R is selected from lower alkyl or chlorinated groups. The molar ratios above do not include the extra chlorine that is required if R reacts with the chlorine. An allowance would have to be made for the extra chlorine, with the molar ratio values of chlorine to ether increased accordingly to compensate therefor. Optimum concentrations of pentachloroacetone cannot be attained when ratios of chlorine to ether lower than those defined above are employed; whereas, if ratios higher than the ratios defined above are employed, the pentachloroacetone will increasingly be destroyed by its further chlorination.

Following the chlorination of the isopropyl ether, the aqueous and organic phases are separated. Most of the pentachloroacetone is contained in the organic phase and can be separated by known methods for the separation of liquid mixtures such as distillation. The pentachloroacetone contained in the aqueous phase can be recovered by known methods, such as extraction, if desired.

To produce the dichloroacetic acid by the process of this invention the pentachloroacetone, whether still contained in the organic phase or separated, is converted to a salt of dichloroacetic acid by reaction with an inorganic base-acting material selected from the group consisting of alkali metal hydroxides, alkaline earth metal hydroxides, alkali metal carbonates, and mixtures thereof. The reaction of the pentachloroacetone with the base-acting material is carried out in the presence of water of sufficient quantity to maintain the added base and the salt formed in solution. An excess of water over this amount will lead to less efficient recovery of the dichloroacetic acid in subsequent steps. It is preferable to add base at a rate sufficient to maintain an excess and to thereby provide a basic reaction medium at all times. It is preferable to add base at a rate sufficient to maintain a rapid rate of reaction. While not critical, it is preferable to maintain the temperature from about 25° to about 50° C. It is also preferable to maintain only a small excess of base, avoiding a large excess which may lead to destruction of some of the dichloroacetate product.

After the reaction with the base-acting material is complete, the aqueous phase of the mixture will contain substantially all of the dichloroacetic acid salt product. The organic phase will contain a small amount of this salt which can be recovered by known methods if desired.

The aqueous solution is acidified with an excess of strong mineral acid, such acid being sufficient to neutralize the base-acting material in the solution and to convert the dichloroacetic acid salt to dichloroacetic acid.

The dichloroacetic acid thus produced can then be recovered from the reaction mixture by known methods. One preferred method for recovering the dichloroacetic acid is extraction, utilizing an organic solvent such as methylene chloride, followed by separation of the organic solvent from the dichloroacetic acid by distillation.

The following example is illustrative of the present invention, but is not to be construed as limiting the scope thereof in any manner.

EXAMPLE

To a flask provided with a heater, a stirrer and a reflux condenser was added 330 ml of water and 187 grams (1.1 moles) of a mixture containing 70 wt.% di(chloroisopropyl) ether, 25 wt.% chloroisopropyl chloropropyl ether and 5 wt.% di(chloropropyl) ether. The mixture was heated to its boiling point, stirred, irradiated with utraviolet light, and gaseous chlorine was fed into the mixture at a rate such that it would react with the mixture without any substantial amount of the chlorine being carried out of the reaction mixture by the product HCl gas. Any chlorine off-gas from the condenser was liquified and returned to the flask. The gaseous HCl was recovered in a scrubber. About 350 g. of chlorine was used. After the reaction was complete, the reaction mixture was cooled and the aqueous and organic phases were separated by using a separatory funnel.

The organic phase was washed with 50 ml. of water, and the washings added to the aqueous phase. The organic phase was then distilled under a reduced pressure of 20 torr and three fractions were collected at overhead temperatures of 40°, 81°–85° C, and 90° C. The volume of the first fraction was 7 ml., 90% of which was 1,1,1-trichloroacetone. The volume of the second fraction was 14 ml., 75% of which was 1,1,1-trichloroacetone and 25% of which was pentachloroacetone. The volume of the third fraction was 123 ml., 95% of which was pentachloroacetone. The total amount of pentachloroacetone gathered in these three fractions was 197 g. and the distillation residue, 35 ml., was a complex mixture of esters and chloroethers.

The aqueous phase from the reaction mixture was extracted ten times with 50-ml. portions of toluene and ten times with 50-ml. portions of methylene chloride. The extracts were combined and distilled, and at a temperature of 65° C and a pressure of 5 torr, a fraction of 22 ml. was obtained, 90% of which was pentachloroacetone. The residue contained 13 ml., 75% of which was pentachloroacetone and 25% dichloroacetic acid. The total pentachloroacetone obtained from the aqueous phase was 52 grams. Five grams of dichloroacetic acid was also obtained. The 5 grams of dichoroacetic acid represented a 2.2% yield based on the chloroisopropyl ether content of the starting material.

The total amount of pentachloroacetone obtained from the organic and aqueous phases was 249 grams for a yield of 60.5% based on the amount of chloroisopropyl radicals in the starting material. In addition 34 g. of carbon tetrachloride and 9 g. of chloroform were recovered.

A mixture of 700 ml of water and 118 g (0.51 mole) of the pentachloroacetone produced was stirred vigorously while 10% aqueous sodium hydroxide was added in small portions. The temperature was kept below 30° and increments of the alkali were added until the solution remained alkaline for four hours. Twenty-nine grams of sodium hydroxide was required. The phases were then separated, the organic phase being extracted twice with portions of the 10% sodium hydroxide. The washings were then added to the aqueous phase. The organic phase was about 98% chloroform with a mass of 48 grams. By extracting the aqueous phase with 50 ml. of methylene chloride, an additional 8 g. of chloroform was obtained for a total of 56 g.

The aqueous phase was then acidified with 75 ml. of concentrated hydrochloric acid and continuously extracted with methylene chloride until evaporation of a portion of fresh extract showed negligible residue. Evaporation of the total methylene chloride extract left a residue of 61 g. (0.47 mole) of dichloroacetic acid having a purity of greater than 95%, providing a yield of 92.

Based on the amount of the chloroisopropyl radicals in the mixture of ethers used, the overall yield of the dichloroacetic acid was 58%.

We claim:

1. A process for preparing dichloroacetic acid which comprises:

reacting chlorine in the presence of water with at least one isopropyl ether having the formula $C_3H_{(7-x)}Cl_x$—O—$C_3H_{(7-y)}Cl_y$ or the formula $C_3H_{(7-x)}Cl_x$—O—R, where $x$ and $y$ are integers independently selected from zero to five and R is selected from lower alkyl groups or chloroinated lower alkyl groups at a temperature of from about 25° to about 300°C. and a pressure of from about 0.5 to about 10 atmospheres to produce pentachloroacetone;

reacting the thus formed pentachloroacetone with a base-acting material selected from the group consisting of alkali metal hydroxides, alkaline earth metal hydroxides, alkali metal carbonates, and mixtures thereof, to produce a salt of dichloroacetic acid; and reacting the thus produced salt of dichloroacetic acid with a mineral acid to produce dichloroacetic acid.

2. The process of claim 1 wherein the temperature during the chlorination step is from about 100° C to about 200° C and the pressure during such step is from about 1 to about 5 atmospheres.

3. The process of claim wherein the chlorination step is carried out under reflux conditions.

4. The process of claim 1 wherein in reacting chlorine in the presence of water with at least one isopropyl ether having the chemical formula $C_3H_{(7-x)}Cl_x$—O—$C_3H_{(7-y)}Cl_y$ where $x$ and $y$ are integers independently selected from zero to five, the molar ratio of chlorine to ether is from about $0.8[(6-x)+(6-y)]:1$ to about $2[(6-x)+(6-y)]:1$ where the $x$ and $y$ in the ratio have the same values as the $x$ and $y$ of the chemical formula.

5. The process of claim 1, wherein the step of reacting chlorine in the presence of water (the chlorination step) with at least one isopropyl ether having the chemical formula $C_3H_{(7-x)}Cl_x$—O—$C_3H_{(7-y)}Cl_y$ where $x$ and $y$ are integers independently selected from zero to five, the molar ratio of chlorine to ether is from about $[(6-x)+(6-y)]:1$ to about $1.4[(6-x)+(6-y)]:1$ where the $x$ and $y$ of the ratio have the same values as the $x$ and the $y$ of the chemical formula.

6. The process of claim 1 wherein in reacting chlorine in the presence of water with at least one isopropyl ether having the chemical formula $C_3H_{(7-x)}Cl_x$—O—R where $x$ is an integer selected from zero to five, the molar ratio of chlorine to ether for the isopropyl group of the ether is from about $0.8(6-x):1$ to about $2(6-x):1$ with $x$ being the same in the ratio as it is the chemical formula.

7. The process of claim 1 wherein in reacting chlorine in the presence of water with at least one isopropyl ether having the chemical formula $C_3H_{(7-x)}Cl_x$—O—R where $x$ is an integer selected from zero to five, the molar ratio of chlorine to the ether, for the isopropyl part of the ether, is from about $(6-x):1$ to about $1.4(6-x):1$ with the $x$ of the ratio having the same value as the $x$ of the chemical formula.

8. The process of claim 1 wherein the reacting mixture is irradiated with ultraviolet light and intimately admixed.

9. The process of claim 1 wherein the ether used is di(chloroisopropyl) ether.

10. A process for preparing dichloroacetic acid which comprises:

A. reacting chlorine in the presence of water with at least one isopropyl ether having the formula $C_3H_{(7-x)}Cl_x$—O—$C_3H_{(7-y)}Cl_y$ or the formula $C_3H_{(7-x)}Cl_x$—O—R, where $x$ and $y$ are integers independently selected from zero to five inclusively and R is selected from lower alkyl groups or chlorinated lower alkyl groups, at a temperature of from about 25° to about 300° C, a pressure of from about 0.5 to about 10 atmospheres, for a time greater than about two hours and with a water to ether volume ratio from about 0.2 to 1 to about 10 to 1 to produce pentachloroacetone;

B. reacting the thus formed pentachloroacetone by contacting it with a base-acting material selected from the group consisting of alkali metal hydroxides, alkaline earth metal hydroxides, alkali metal carbonates, and mixtures thereof with the base-acting material being added at a rate sufficient to provide a basic reaction medium at all times, sufficient water being present to maintain the added base and the salt formed in solution, with the reaction being carried out at a temperature of from about 25° to about 50° C to produce a salt of dichloroacetic acid; and C. reacting the salt of the dichloroacetic acid with a strong mineral acid to form dichloroacetic acid.

11. The process of claim 10 wherein the chlorination reaction is carried out at from about 100° to 200° C and a pressure of from about 1 to about 5 atmospheres.

12. The process of claim 10 wherein in reacting chlorine in the presence of water with at least one isopropyl ether having the chemical formula $C_3H_{(7-x)}Cl_x-O-C_3H_{(7-y)}Cl_y$ where $x$ and $y$ are integers independently selected from zero to five, the molar ratio of chlorine to ether is from about $0.8[(6-x)+(6-y)]:1$ to about $2[(6-x)+(6-y)]:1$ where the $x$ and $y$ in the ratio have the same values as the $x$ and $y$ of the chemical formula.

13. The process of claim 10, wherein in the step of reacting chlorine in the presence of water (the chlorination step) with at least one isopropyl ether having the chemical formula $C_3H_{(7-x)}Cl_x-O-C_3H_{(7-y)}Cl_y$ where $x$ and $y$ are integers independently selected from zero to five, the molar ratio of chlorine to ether is from about $[(6-x)+(6-y)]:1$ to about $1.4[(6-x)+(6-y)]:1$ where the $x$ and $y$ of the ratio have the same values as the $x$ and the $y$ of the chemical formula.

14. The process of claim 10 wherein in reacting chlorine in the presence of water with at least one isopropyl ether having the chemical formula $C_3H_{(7-x)}Cl_x-O-R$ where $x$ is an integer selected from zero to five, the molar ratio of chlorine to ether for the isopropyl group of the ether is from about $0.8(6-x):1$ to about $2(6-y):1$ with $x$ being the same in the ratio as it is in the chemical formula.

15. The process of claim 10 wherein in reacting chlorine in the presence of water with at least one isopropyl ether having the chemical formula $C_3H_{(7-x)}Cl_x-O-R$ where $x$ is an integer selected from zero to five, the molar ratio of chlorine to the ether, for the isopropyl part of the ether, is from about $(6-x):1$ to about $1.4(6-x):1$ with the $x$ of the ratio having the same value as the $x$ of the chemical formula.

16. The process of claim 10 wherein the water to ether volume ratio is from about 0.5 to 1 to about 2.5 to 1.

17. The process of claim 10 wherein the chlorination step is carried out under reflux conditions.

18. The process of claim 10 wherein the isopropyl ether used is di(chlorisopropyl) ethers.

19. The process of claim 10 wherein the base-acting material is an alkali metal hydroxide or an alkaline earth metal hydroxide.

20. The process of claim 10 wherein the base-acting material used is an alkali metal carbonate.

21. A process for the production of pentachloroacetone comprising reacting chlorine in the presence of water with at least one isopropyl ether having the formula $C_3H_{(7-x)}Cl_x-O-C_3H_{(7-y)}Cl_y$
or the formula $C_3H_{(7-x)}Cl_x-O-R$, where $x$ and $y$ are integers independently selected from zero to five and R is selected from lower alkyl groups of chlorinated lower alkyl groups at a temperature of from about 25° to about 300° C and a pressure from about 0.5 to about 10 atmospheres.

22. The process of claim 21 wherein the temperature during the chlorination is from about 100° to about 200° C and the pressure is from about 1 to about 5 atmospheres.

23. The process of claim 21 wherein the chlorination is carried out under reflux conditions.

24. The process of claim 21 wherein in reacting chlorine in the presence of water with at least one isopropyl ether having the chemical formula $C_3H_{(7-x)}Cl_x-O-C_3H_{(7-y)}Cl_y$ where $x$ and $y$ are integers independently selected from zero to five, the molar ratio of chlorine to ether is from about $0.8[(6-x)+(6-y)]:1$ to about $2[(6-x)+(6-y)]:1$ where the $x$ and $y$ in the ratio have the same values as the $x$ and $y$ of the chemical formula.

25. The process of claim 21, wherein the step of reacting chlorine in the presence of water (the chlorination step) with at least one isopropyl ether having the chemical formula $C_3H_{(7-x)}Cl_x-O-C_3H_{(7-y)}Cl_y$ where $x$ and $y$ are integers independently selected from zero to five, the molar ratio of chlorine to ether is from about $[(6-x)+(6-y)]:1$ to about $1.4[(6-x)+(6-y)]:1$ where the $x$ and $y$ of the ratio have the same values as the $x$ and the $y$ of the chemical formula.

26. The process of claim 21 wherein in reacting chlorine in the presence of water with at least one isopropyl ether having the chemical formula $C_3H_{(7-x)}Cl_x-O-R$ where $x$ is an integer selected from zero to five, the molar ratio of chlorine to ether for the isopropyl group of the ether is from about $0.8(6-x):1$ to about $2(6-x):1$ with $x$ being the same in the ratio as it is the chemical formula.

27. The process of claim 21 wherein in reacting chlorine in the presence of water with at least one isopropyl ether having the chemical formula $C_3H_{(7-x)}Cl_xCl_x-O-R$ where $x$ is an integer selected from zero to five, the molar ratio of chlorine to the ether, for the isopropyl part of the ether, is from about $(6-x):1$ to about $1.4(6-x):1$ with the $x$ of the ratio having the same value as the $x$ of the chemical formula.

28. The process of claim 21 wherein the reaction is carried out at from 100° to about 200° C and a pressure of from about 1 to about 5 atmospheres.

29. The process of claim 21 wherein the ether used is a mixture of ethers comprising di(chloroisopropyl) ether, chloroisopropyl chloropropyl ether and dichloropropyl ether.

30. The process of claim 29 wherein the chlorine to ether mole ratio is from about 14 to 1 to about 10 to 1.

31. The process of claim 29 wherein the water to ether volume ratio is from about 0.5 to 1 to about 2.5 to 1.

32. The process of claim 29 wherein the reaction is carried out in the presence of actinic light and the chlorine, water, and ethers are intimately admixed.

* * * * *

UNITED STATES PATENT AND TRADEMARK OFFICE
CERTIFICATE OF CORRECTION

PATENT NO. : 3,996,272
DATED : December 7, 1976
INVENTOR(S) : J. D. Burger and W. L. Howard It is certified that error appears in the above-identified patent and that said Letters Patent are hereby corrected as shown below:

Col. 1, line 65 "aboout" should be --- about ---.

Col. 2, line 27 "1.4](" should be ---1.4[( ---.

Col. 4, line 49 after 0.5 insert --- to ---.

Col. 9, line 54 "of" should be --- or ---.

Col. 10, line 36 delete the last $Cl_x$.

Signed and Sealed this

Twelfth Day of April 1977

[SEAL]

Attest:

RUTH C. MASON
Attesting Officer

C. MARSHALL DANN
Commissioner of Patents and Trademarks